United States Patent
Setier et al.

(10) Patent No.: US 10,066,247 B2
(45) Date of Patent: Sep. 4, 2018

(54) PROCESS FOR PRODUCING AN ORGANIC PRODUCT FROM A CARBON-BASED MATTER FEEDSTOCK USING GASIFICATION FOLLOWED BY FERMENTATION OF THE SYNTHESIS GAS

(71) Applicant: Commissariat A L'Energie Atomique Et Aux Energies Alternatives, Paris (FR)

(72) Inventors: Pierre-Alexandre Setier, Bourgoin-Jallieu (FR); Florian Delrue, Pertuis (FR)

(73) Assignee: Commissariat A L'Energie Atomique Et Aux Energies Alternatives, Paris (FR)

( * ) Notice: Subject to any disclaimer, the term of this patent is extended or adjusted under 35 U.S.C. 154(b) by 0 days.

(21) Appl. No.: 15/030,932

(22) PCT Filed: Oct. 22, 2014

(86) PCT No.: PCT/IB2014/065547
§ 371 (c)(1),
(2) Date: Apr. 21, 2016

(87) PCT Pub. No.: WO2015/059656
PCT Pub. Date: Apr. 30, 2015

(65) Prior Publication Data
US 2016/0265008 A1   Sep. 15, 2016

(30) Foreign Application Priority Data
Oct. 24, 2013   (FR) ..................................... 13 60398

(51) Int. Cl.
| | |
|---|---|
| *C12P 7/04* | (2006.01) |
| *C12P 7/08* | (2006.01) |
| *C12P 7/14* | (2006.01) |
| *C12P 7/40* | (2006.01) |
| *C12P 7/52* | (2006.01) |
| *C12P 7/54* | (2006.01) |
| *C12M 1/00* | (2006.01) |

(52) U.S. Cl.
CPC .............. *C12P 7/54* (2013.01); *C12M 43/00* (2013.01); *C12M 47/10* (2013.01); *C12P 7/04* (2013.01); *C12P 7/08* (2013.01); *C12P 7/14* (2013.01); *C12P 7/40* (2013.01); *C12P 7/52* (2013.01)

(58) Field of Classification Search
CPC ....... Y02E 50/17; Y02E 20/326; Y02E 50/13; Y02E 50/343; Y02E 50/346; Y02E 50/10; B01D 2251/95; B01D 2257/504; B01D 53/62; B01D 53/84; C10G 2300/1011; C10G 2300/4043; C10G 2300/405; C10L 1/026; C12N 1/20; C12N 1/12; C12M 43/00; C12M 47/10; C12M 23/26; C12M 29/06; C12M 41/00; C12M 41/18; C12M 43/02; C12M 43/08; C12M 21/02; C12P 7/40; C12P 7/08; C12P 7/14; C12P 7/52; C12P 7/54; C12P 7/04; C01C 1/04; C07C 1/04; C07C 67/02; E21B 43/16
See application file for complete search history.

(56) References Cited

U.S. PATENT DOCUMENTS

| | | | |
|---|---|---|---|
| 2012/0003705 A1* | 1/2012 | Jin .......................... | B01D 53/62 435/136 |
| 2013/0164802 A1* | 6/2013 | Hickey ..................... | C12P 7/08 435/140 |
| 2013/0189750 A1* | 7/2013 | Jin .......................... | B01D 53/62 435/140 |

OTHER PUBLICATIONS

Pradeep Chaminda Munasinghe and Samir Kumar Khanal, "Biomass-derived syngas fermentation into biofuels: Opportunities and challenges." Bioresource Technology, Elsevier Ltd., www.elsevier.com/locate/biotech. pp. 5013-5022, Dec. 9, 2009.

* cited by examiner

*Primary Examiner* — Deborah K Ware
(74) *Attorney, Agent, or Firm* — Cooper Legal Group LLC; Ronald Kachmarik

(57) ABSTRACT

The invention relates to a process for producing a fuel, in particular a liquid fuel, or another organic product, from a carbon-based matter feedstock, comprising the following steps: a/ gasification of the carbon-based matter feedstock in a first reactor, termed gasifier (1), b/ downstream of the gasification, fermentation of the synthesis gas produced according to step a/, by means of microorganisms, water and nutrients in a second reactor, termed fermenter (2), c/ recovery, downstream of the fermenter, of the microorganisms and of the water, d/ injection of at least a part of the recovered microorganisms and, where appropriate, of at least a part of the recovered water at the inlet (10) of the gasifier.

13 Claims, 1 Drawing Sheet

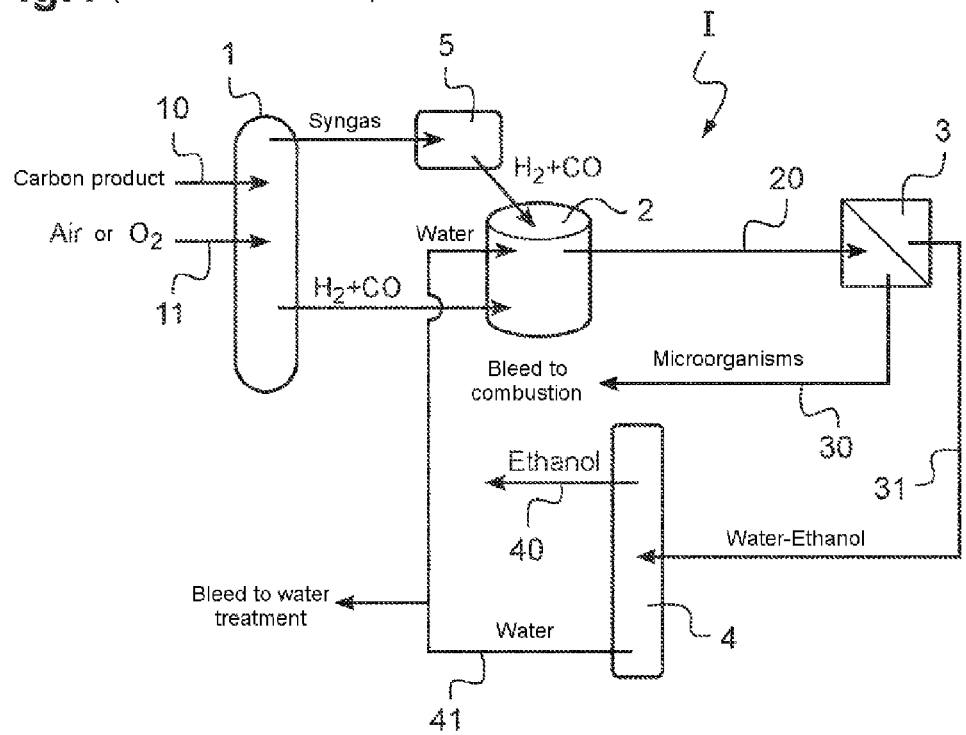
Fig.1 (STATE OF THE ART)
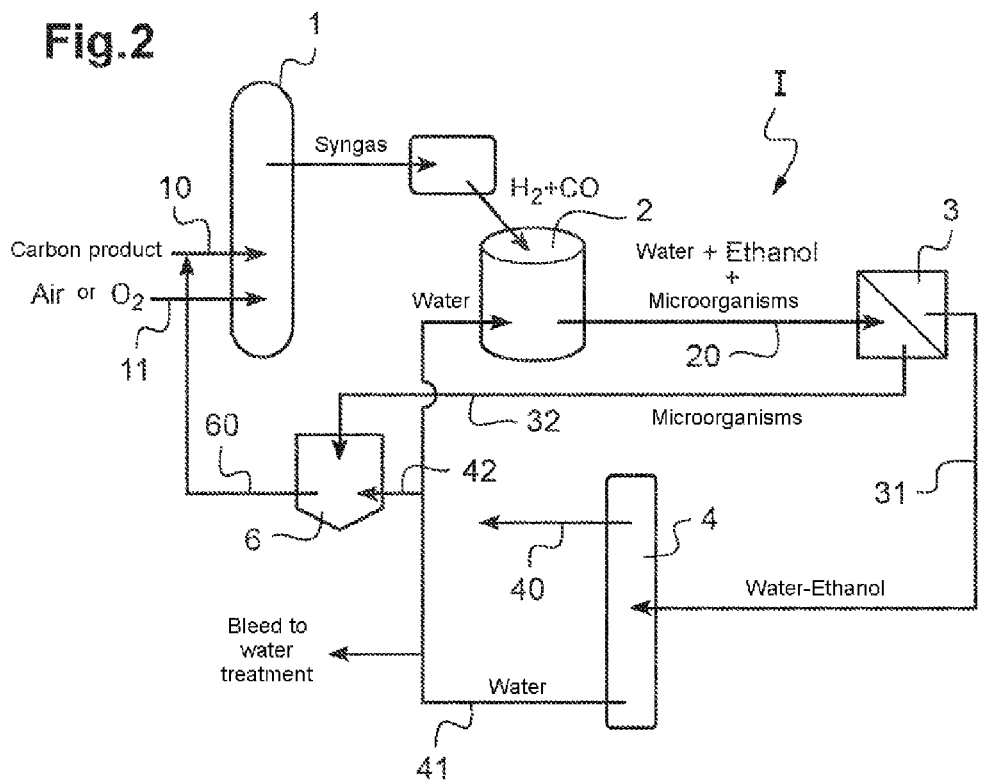
Fig.2

PROCESS FOR PRODUCING AN ORGANIC PRODUCT FROM A CARBON-BASED MATTER FEEDSTOCK USING GASIFICATION FOLLOWED BY FERMENTATION OF THE SYNTHESIS GAS

TECHNICAL FIELD

The present invention relates to a process for the production of an organic product, in particular of a fuel, from a carbon-based matter feedstock, employing a gasification of the carbon-based matter feedstock and a fermentation of the synthesis gas produced by the gasification by means of microorganisms and water.

The term "carbon-based matter feedstock" is understood to mean any matter containing an amount of carbon, in particular any carbon-based matter from waste products, such as coal, petroleum coke, organic waste, plastic waste, and the like.

The invention is targeted at improving the yield of such a process for the production of an organic product.

A preferred application is the production of ethanol or butanol from plastic waste products.

STATE OF THE ART

The gasification of biomass and coal has been known for a long time. Generally, it may be defined as a thermochemical conversion of biomass or coal by the action of heat in the presence of gasifying agent(s). The aim is to generate, on conclusion of the gasification, a "synthesis gas" (syngas) gas mixture which comprises carbon monoxide and hydrogen ($CO+H_2$), inter alia.

Thus, the gasification is an endothermic reaction between the carbon-based matter and the gasifying agent(s) according to the following chemical reactions:

$$C+H_2O \rightarrow CO+H_2 \quad (1)$$

$$C+CO_2 \rightarrow 2CO \quad (2)$$

The synthesis gas produced is predominantly composed of the gases CO, $CO_2$ and $H_2$.

It also contains minor compounds ($NH_3$, HCl, HF, HCN, $H_2S$, COS, alkali metals, and the like) in the vapor state originating from the carbon-based matter or from the gasifying agent(s). Finally, for low-temperature (850° C.) gasifications, a more or less large portion of hydrocarbon compounds in the gas form (tars, $CH_4$), resulting from an incomplete oxidation of the carbon-based matter, is obtained.

Reactions (1) and (2) have to be favored. It is thus necessary to compensate for the energy lost during these endothermic reactions. The supplying of heat to the gasification reactor (gasifier) is either direct ("autothermal" operating mode), according to which a portion of the carbon-based matter which it is desired to gasify is incinerated, or indirect ("allothermal" operating mode), according to which an external heat source is supplied.

Simple in conception and construction, gasification processes employing a fixed bed or fluidized bed reactor produce a gas of relatively poor quality as result of a relatively high tar content and of a relatively low $H_2/CO$ ratio obtained. However, fluidized bed reactors have the advantage of having a significant experience feedback and being able to be of dimensions compatible with industrial exploitation. Finally, entrained-flow reactors are best suited to the gasification of large volumes of carbon-based matter, the unit power of a gasifier of this type being able to be greater than 50 MWth. As result of the very short residence time of the carbon-based matter feedstock and of the very high operating temperatures, typically of greater than 1400° C., the synthesis gas obtained by entrained-flow gasifiers contains virtually no tars, which has the advantage of avoiding an additional stage of cleaning the synthesis gas.

An advantageous gasification example is that of the gasification of lignocellulose biomass, which makes it possible to generate a synthesis gas and to produce, downstream, either liquid fuels or other organic products. This gasification takes place in the presence typically of steam at approximately 800-900° C. for fluidized bed reactors. Conventionally, such a gasification converts the carbon of biomass with a gas at the outlet of the gasifier having a mean composition of 20-25% of CO, 8-12% of $CH_4$, 18-22% of $CO_2$ and approximately 38-42% of $H_2$ and $C_2$ to $C_{16}$ organic compounds, plus inorganic compounds.

Provision has already been made to carry out the fermentation of synthesis gas using specific microorganisms which are capable of predominantly producing a type of fuel under low temperature and pressure conditions.

These specific microorganisms belong mainly to the family of the anaerobic bacteria of the *Clostridium* genus. For example, some of them could be identified for the conversion of synthesis gas to give ethanol. The majority of these bacteria use the metabolic pathway, known as the Wood-Ljungdahl cycle, or the reductive acetyl-CoA pathway.

For the conversion to give ethanol, the chemical reactions carried out by the bacteria are as follows:

$$6CO+3H_2O \rightarrow C_2H_5OH+4CO_2$$

$$6H_2+2CO_2 \rightarrow C_2H_5OH+3H_2O.$$

A specific reaction medium rich in nutrients (minerals and trace elements, such as metals and vitamins) is used to direct and optimize the energy flow in the desired metabolic pathway, thus maximizing the production of fuel or of organic product desired.

The essential advantages of a synthesis by fermentation using microorganisms, in comparison with a synthesis by the chemical pathway, may be summarized as follows:
  the temperature and pressure operating conditions are less severe,
  the use of microorganisms as biological catalysts makes it possible to tolerate to a larger extent impurities present within the synthesis gas, and also a broader range of $H_2/CO$ ratios.

The main limitations on the fermentation of a synthesis gas are related to the mass transfer between the gas phases and the liquid phases. These limitations are the cause of the relatively modest productive outputs which are observed at the current time.

While these technologies are already arousing great interest for the production of ethanol, indeed even for ethanol/acetone/butanol mixtures, the potential of these fermentation technologies is much greater if recent developments in metabolic engineering and/or synthetic biology are considered.

Thus, it is already recognized that the fermentation of synthesis gas obtained by gasification of carbon-based matter may make it possible, as a function of the microorganisms selected, to obtain different molecules, such as acetate, formate, butyrate, n-butyrate, lactate, pyruvate, ethanol, butanol or acetone and more recently 2,3-butanediol.

The concentration of synthesized organic product in water is low, typically less than 50 g/l for ethanol. The amounts of water necessary for the synthesis by fermentation are thus very high.

Currently, most of this water is reintroduced into the fermenter after distillation both of the fermentation culture medium (water and nutrients) and of the final organic product(s) which it is desired to obtain.

In addition, it proves to be necessary to bleed off a portion of the water in order to retain a restricted level of contaminant in the fermentation medium.

In the same way, only a portion of the culture medium freed from the organic product(s) may be recycled in the fermentor. The other portion is regarded as a waste product and has to be treated as such.

Furthermore, a physical separation between the solids and the liquids, generally by settling and/or filtration, is carried out at the outlet of the fermenter in order to recover the microorganisms, a portion of which may, if appropriate, be recycled in the fermenter. Just as for the culture medium, the other portion of the microorganisms is regarded as a waste product and has to be treated as such. Generally, this portion of the microorganisms forming waste products is incinerated.

Consequently, the amount of microorganisms and of water to be treated in a known process for the production of organic product(s) employing a gasification followed by a fermentation is relatively high and requires a great deal of energy.

There thus exists a need to improve the processes for the production of a fuel or any other organic product employing a gasification followed by a fermentation using microorganisms and water, in particular for the purpose of increasing its material yield and of reducing the energy cost of the treatment of waste products composed of said microorganisms and water.

The general aim of the invention is to partly meet this need.

A specific aim is to provide a process for the production of a fuel or any other organic product employing a gasification followed by a fermentation using microorganisms and water, with an increased material yield, a reduced energy cost for the treatment of waste products composed of said microorganisms and water and, in addition, reduced capital expenditure.

DISCLOSURE OF THE INVENTION

In order to do this, a subject matter of the invention is a process for the production of a fuel, in particular a liquid fuel, or of another organic product, from a carbon-based matter feedstock, comprising the following stages:

a/ gasification of the carbon-based matter feedstock in a first reactor, referred to as gasifier, b/ downstream of the gasification, fermentation of the synthesis gas produced according to stage a/ using microorganisms, water and nutrients in a second reactor, referred to as fermenter, c/ recovery, downstream of the fermenter, of the microorganisms and water, d/ injection of at least a portion of the recovered microorganisms and, if appropriate, of at least a portion of the recovered water at the inlet of the gasifier, and, during the recovery stage c/:

a stage c1/of separation between the microorganisms which have been used for the fermentation and the mixture between the organic product resulting from the fermentation and the water, followed by a distillation of the mixture in order to produce the final organic product, a stage c2/of adjustment of the concentration of water in the microorganisms recovered by the separation.

Thus, the present invention provides a process which may recycle at least a substantial portion of the waste products which it produces (microorganisms and water) directly in the gasifier.

Moreover, this makes it possible to introduce into the gasifier water and additional carbon which is present in the microorganisms and thus to increase the material yield of the overall process.

Moreover, this makes it possible to economize on the treatment of the water and microorganisms. Finally, the present invention makes it possible to perfectly adjust the ratio of the water to the carbon-based matter at the gasifier inlet.

The additional capital expenditure related to the implementation of the present invention in an existing plant is low as, if appropriate, only the installation of additional pipes and of an additional metering device, suitable for adjusting the concentration of water in the microorganisms recovered by the separation, using water recovered from the distillation, is required.

In order to carry out the adjustment stage c2/, it is possible to either introduce water into the gasifier or to introduce more gas in order to compensate for the excess water.

The first possibility is preferred as it is less energy consuming than the second.

The water introduced in the gasifier may originate partly or completely from the distillation stage or it may originate from an external circuit.

Preferably, in order to remove any presence of impurities, such as tar and/or $CO_2$, between the gasification stage a/ and the fermentation stage b/, a stage a1/of cleaning the synthesis gas produced according to stage a/ is carried out.

According to an advantageous embodiment, the microorganisms are mesophilic anaerobic microorganisms, preferably chosen from the following species: *Clostridium jungdahlii, Clostridium carboxidovorans P7, Clostridium autoethanogenum, Eurobacterium limosum, Rhodospirillum rubrum, Peptostreptococcus productus, Acetobacterium woodii* or *Butyribacterium methylotrophicum*. More generally, all the microorganisms cited in tables 2 and 3 of the publication [1] may advantageously be used.

The separation stage c1/is preferably carried out by microfiltration or by coagulation/flocculation using a flocculating agent based on an organic polymer, such as polyamine or polyacrylamide, followed by separation by settling or by floatation.

According to this alternative form, for a concentration of microorganisms recovered by the separation of between 100 and 250 grams/liter of concentrate, the adjustment according to stage c2/is preferably carried out so to obtain a concentration of microorganisms to be injected into the gasifier of between 20 and 100 grams/liter of solution.

The gasification reaction may advantageously be carried out at temperatures of 700 and 1600° C.

According to a first alternative form, the gasifier is a reactor of fluidized bed type, the gasification reaction being carried out at temperatures of between 800 and 950° C.

According to a second alternative form, the gasifier is a reactor of entrained-flow type, the gasification reaction being carried out at temperatures of between 1400 and 1600° C.

The organic product obtained by the process according to the invention may be chosen from acetate, formate, butyrate, n-butyrate, lactate, pyruvate, ethanol, butanol or acetone and more recently 2,3-butanediol.

The invention also relates, under another of its aspects, to a plant for the continuous production of a fuel, in particular a liquid fuel, or of another organic product from a carbon-based matter feedstock comprising:
a gasifier,
a fermenter, downstream of the gasifier, comprising within it microorganisms, water and nutrients appropriate for carrying out the fermentation of the synthesis gas produced by the gasifier,
means for recovery of at least a portion of the microorganisms and water, downstream of the fermenter; the recovery means being connected to the inlet of the gasifier so as to inject at least a portion of the recovered microorganisms and, if appropriate, at least a portion of the recovered water,
the recovery means comprising:
a device for separation between the microorganisms and the mixture between the organic product resulting from the fermentation and the water which has been used for the fermentation within the fermenter,
a metering device, downstream of the separation device and of a device for distillation of the mixture, appropriate for adjusting the concentration of water in the microorganisms recovered by the separation.

According to an advantageous embodiment, the separation device comprises at least one filtration membrane, the size of the pores of which is suited to the size of the microorganisms used in the fermentation stage b/, preferably of between 0.1 and 10μm.

By adjusting the effectiveness of the filtration by the filtration membrane, it is possible to fix the content of water in the concentrate of microorganisms. If this proves to be insufficient, in particular in the event of a need for more water for the gasification if the carbon-based matter is highly charged in carbon, for example, it is preferable to add water originating from the distillation stage.

Finally, the invention relates to a preferred application of the process which has just been described or of the plant which also has just been described for producing ethanol or butanol from plastic waste products.

BRIEF DESCRIPTION OF THE DRAWINGS

Other advantages and characteristics of the invention will more clearly emerge on reading the detailed description of the invention, given by way of illustration and without limitation, with reference to the following figures, among which:

FIG. 1 is a diagrammatic view of the principle of a plant for the production of ethanol from a carbon-based matter feedstock continuously employing a gasification followed by a fermentation using microorganisms according to the state of the art;

FIG. 2 is a diagrammatic view of the principle of a plant for the production of ethanol from a carbon-based matter feedstock continuously employing a gasification followed by a fermentation using microorganisms according to the present invention.

DETAILED DESCRIPTION

Throughout the patent application and in particular in the description which will follow, the terms "inlet", "outlet", "upstream" and "downstream" are used with reference to the direction of transfer of the carbon-based matter feedstock and of the synthesis gas in the plant for the production of an organic product, such as ethanol, employing the process according to the invention.

It is specified that the keys given in FIGS. 1 and 2, and in particular the reactors and devices indicated, are only done so by way of nonlimiting example.

It is specified that, for the sake of clarity, the same elements in a plant for the production of ethanol according to the state of the art and a plant for the production of ethanol according to the invention are designated by the same references.

As illustrated in FIG. 1, the continuous plant I employs a process for a gasification of a carbon-based matter feedstock according to the state of the art followed by a fermentation using microorganisms for the synthesis of ethanol.

Thus, the plant I comprises first of all a gasification reactor or gasifier 1, of fluidized bed type, continuously fed at its inlet 10, for example with plastic waste products from a storage tank (not represented). The fluidized bed reactor 1 may preferably operate between 800 and 950° C. The reactor 1 may also be a reactor of entrained-flow type (entrained-flow reactor or EFR) preferably operating at temperatures typically of between 1400 and 1600° C.

The gasifier 1 is also supplied at its inlet 11 with gasifying agents, for example air or oxygen.

At the outlet of the gasification reactor 1, a crude synthesis gas mixture comprising CO, $CO_2$, $H_2O$ and $H_2$ as the predominant entities is emitted.

The synthesis gas mixture may be subjected to cleaning in an appropriate device 5 in order to extract the contaminants or the gases which inhibit the microorganisms of the fermenter 2.

The cleaned synthesis gas is then sent to a bioreactor 2 or fermenter employing a fermentation using mesophilic anaerobic microorganisms, water and nutrients present within the fermenter 2, which produces ethanol according to the reactions:

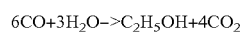

The water, the ethanol produced and the microorganisms which have been used in the fermentation are then extracted at the outlet of the fermenter 2 and sent via a line 20 to a solid/liquid separation device 3 comprising at least one microfiltration membrane, i.e. the pores of which have a size of between 0.1 and 10 μm.

The solids composed of the microorganisms thus separated are then subjected to bleeding 30 in order to be incinerated by combustion.

The separated liquid mixture composed of the water and of the ethanol synthesized is for its part sent via a line 31 to a distillation device 4.

The distilled ethanol is recovered at the outlet 40 of the distillation device 4. It constitutes the final product which may be used.

The distilled water is recovered at the outlet 41 of the distillation device 4 and, for a major part, recycled by being reinjected at the inlet of the fermenter 2 and, for the remaining part, sent to a water treatment unit (not represented).

In order to increase the material yield and to reduce the energy cost for the treatment of waste products composed of said microorganisms and water in the plant according to the state of the art represented in FIG. 1, the inventors have thought of reinjecting the microorganisms recovered and, if appropriate, at least a portion of the water recovered at the inlet 10 of the gasifier 1.

Thus, as shown in FIG. 2, in a plant I in accordance with the invention, there is first of all provided, at the outlet of the separation device 3, a line 32 for recovery of the recovered microorganisms which feeds the inlet of a metering device 6.

The plant I in accordance with the invention also comprises a line 42 for at least a portion of the water resulting from the distillation 4 which will also supply the inlet of the metering device 6.

Thus, the metering device 6, downstream of the separation device 3 and of the device 4 for distillation of the mixture, makes it possible, using the water recovered from the distillation, to adjust the concentration of water in the microorganisms recovered by the separation.

The outlet of the metering device 6 is connected to the inlet 10 of the gasifier 1 using the line 60 in order to supply the gasifier with microorganisms thus recycled and with water thus recycled.

Thus, the plant I according to the invention represented in FIG. 2 exhibits, in comparison with the plant according to the state of the art represented in FIG. 1, the following advantages:

retreatment of the fermentation waste products, at a low energy cost;
retreatment of the water resulting from the fermentation in the gasification stage, this water being subtracted, if necessary, from gasifying agent;
increase in the material yield;
perfect adjustment of the water/carbon-based matter ratio for the gasification 1.

The inventors have performed the initial calculations of gain in material yield.

The data are as follows:
Water/Carbon-Based Matter Feedstock Ratio: from 0% to 50%;
Concentration of Microorganisms During the Synthesis 2: from 0.5 to 2 g/l of medium;
Concentration of Microorganisms for the Recycling Loop 32, 6, 60: from 20 to 100 g/l.

Assuming a throughput of carbon-based matter feedstock of 1 t/h, the production of the organic product, such as ethanol, may be advantageously between 200 and 500 t/h with a throughput of microorganisms to be retreated then of between 10 and 20 kg/h.

Thus, an increase in yield by weight of the order of 1.5% is obtained.

Although described with reference exclusively to ethanol, the production plant may be used to obtain another organic product made of a fuel, in particular a liquid fuel, or another synthesis product and may be used for production from any type of carbon-based matter feedstock (coal, petroleum coke, organic waste, plastic waste, and the like).

REFERENCE CITED

[1]: "Biomass-derived syngas fermentation into biofuels: Opportunities and challenges" by P. C. Munasinghe and S. K. Khanal, Department of Molecular Biosciences and Bioengineering (MBBE), University of Hawai'i at Manoa, Agricultural Science, Bioresource (impact factor: 4.25). July 2010; 101 (13):5013-22. DOI:10.1016/j.biortech.2009.12.098.

The invention claimed is:

1. A process for the production of a liquid organic fuel product from a carbon-based matter feedstock, comprising the following stages:
a/ gasification of the carbon-based matter feedstock in a first gasification reactor to produce a synthesis gas,
b/ downstream of the gasification, fermentation of the synthesis gas produced according to stage a/ using microorganisms, water and nutrients in a fermenter to produce a mix comprising an organic product,
c/ recovery, downstream of the fermenter, of the microorganisms and water,
d/ injection of at least a portion of the recovered microorganisms or, of at least a portion of the recovered microorganisms and of at least a portion of the recovered water, at the inlet of the first gasification reactor, and, during the recovery stage c/:
a stage c1/ of separation between the microorganisms which have been used for the fermentation and the mixture between the organic product resulting from the fermentation and the water, followed by a distillation of the mixture in order to produce the liquid organic fuel product,
a stage c2/ of adjustment of the concentration of water in the microorganisms recovered by the separation.

2. The production process as claimed in claim 1, according to which, between the gasification stage a/ and the fermentation stage b/, a stage a1/ of cleaning the synthesis gas produced according to stage a/ is carried out.

3. The production process as claimed in claim 1, according to which the microorganisms are mesophilic anaerobic microorganisms chosen from the following species: *Clostridium jungdahlii, carboxidovorans P7, Clostridium autoethanogenum, Eurobaeterium lintosum, Rhodospirillum rubrum, Pepiostreptoeoecus productus, Aceiobacterium woodii* or *Buoxibacterium methyloirophicurn*.

4. The production process as claimed in claim 1, the separation stage c1/ is carried out by microfiltration or by coagulation/flocculation using a flocculating agent based on an organic polymer chosen from polyamine or polyacrylamide, followed by settling or by floatation.

5. The production process as claimed in claim 1, according to which a concentration of microorganisms recovered by the separation is between 100 and 250 grams/liter of concentrate, the adjustment according to stage c2/ is carried out to obtain a concentration of microorganisms of between 20 and 100 grams/liter of solution to be injected into the first gasification reactor.

6. The production process as claimed in claim 1, according to which the gasification reaction is carried out at temperatures of 70 and 1600° C.

7. The production process as claimed in claim 1, according to which the first gasification reactor is a fluidized bed reactor, the gasification reaction being carried out at temperatures of between 800 and 950° C.

8. The production process as claimed in claim 1, according to which the first gasification reactor is an entrained-flow reactor, the gasification reaction being carried out at temperatures of between 1400 and 1600° C.

9. The production process as claimed in claim 1, wherein the liquid organic fuel product produced at the separation stage c1/ is chosen from acetate, formate, butyrate, ethanol, butanol, acetone, or 2,3-butanediol.

10. The production process as claimed in claim 1, the liquid organic fuel product being a liquid fuel.

11. A plant for the continuous production of a liquid organic fuel product from a carbon-based matter feedstock comprising:

a first gasification reactor having an inlet, a fermenter, downstream of the first gasification reactor, comprising microorganisms, water and nutrients for carrying out fermentation of the synthesis gas produced by the first gasification reactor, means for recovery of at least a portion of the microorganisms and water, downstream of the fermenter; the recovery means being connected to the inlet of the first gasification reactor so as to inject at least a portion of the recovered microorganisms or, at least a portion of the recovered microorganisms and at least a portion of the recovered water into the inlet, the recovery means comprising:

a device for separation between the microorganisms and a mixture comprising liquid organic fuel product resulting from the fermentation and the water which has been used for the fermentation within the fermenter, a metering device, downstream of the separation device, and a device for distillation of the mixture, and the device for adjusting the concentration of water in the microorganisms recovered by the separation.

12. The plant as claimed in claim 11, the separation device comprising at least one filtration membrane having the size of the pores of which is suited to the size of the microorganisms used in the fermenter, said size of the pores is between 0.1 and 10 µm.

13. The plant as claimed in claim 11 for production of methanol or ethanol from plastic waste products.

\* \* \* \* \*